United States Patent [19]

Rivier et al.

[11] Patent Number: 4,677,193

[45] Date of Patent: Jun. 30, 1987

[54] PEPTIDES CONTAINING AN ALIPHATIC-AROMATIC KETONE SIDE CHAIN

[75] Inventors: Jean E. F. Rivier, LaJolla; Harry A. Anderson, San Diego; Wylie W. Vale, Jr., LaJolla, all of Calif.

[73] Assignee: The Salk Institute for Biological Studies, San Diego, Calif.

[21] Appl. No.: 704,299

[22] Filed: Feb. 22, 1985

[51] Int. Cl.$^4$ .............................................. C07K 7/20
[52] U.S. Cl. .................................................. 530/313
[58] Field of Search ................. 260/112.5 R; 530/313

[56] References Cited

U.S. PATENT DOCUMENTS 4,118,483 10/1978 Konig et al. ........................ 514/15

OTHER PUBLICATIONS

George A. Olah, "Friedel–Crafts & Related Reactions", 1963, pp. 189–191, 317–323.
"The Peptides", 1980, vol. 2, Chap. 1, Barany et al., pp. 192–198.
von Walter Keller–Schierlein et al., Helvetica Chemica Acta, vol. 63, Fasc. 1, 1980, pp. 250–254.

*Primary Examiner*—Delbert R. Phillips
*Attorney, Agent, or Firm*—Fitch, Even, Tabin & Flannery

[57] ABSTRACT

GnRH peptide analogs which regulate the secretion of gonadotropins by the pituitary gland and either promote or inhibit the release of steroids by the gonads. Administration of an effective amount of a GnRH antagonist prevents ovulation of female mammalian eggs and/or the release of gonadotropins. Administration of GnRH agonists can be used to regulate fertility in male and female mammals.

These and other peptide hormones exhibit improved binding efficiency and biological potency as a result having a residue in a critical, generally central location in the chain which residue contains a mixed alkyl ketone side-chain terminating in an aromatic group. Methods for efficiently synthesizing these peptides from readily available compounds are disclosed.

4 Claims, No Drawings

PEPTIDES CONTAINING AN ALIPHATIC-AROMATIC KETONE SIDE CHAIN

This invention was made with Government support under Contract Nos. HD-22824 and HD-42833 and Grant No. HD-13527 awarded by the National Institutes of Health. The Government has certain rights in this invention.

The present invention relates to peptides which affect the release of gonadotropins or inhibit the release of GH by the pituitary gland in mammalians, and to methods of making such peptides. More particularly, the present invention is directed to peptides which have improved biological potency to either promote or inhibit gonadal function and the release of the steroidal hormones, progesterone and testosterone or improved biological potency to inhibit the release of GH.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes. Growth hormone(GH) is also released by the pituitary gland.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure: pGlu-His-Trp-Ser-Tyr-Gly-Leu-Arg-Pro-Gly-$NH_2$.

Peptides are compounds which contain two or more amino acids in which the carboxyl group of one acid is linked to the amino group of the other acid. The formula for GnRH, as represented above, is in accordance with conventional representation of peptides where the amino or N-terminus appears to the left and the carboxyl or C-terminus to the right. The position of the amino acid residue is identified by numbering the amino acid residues from left to right. In the case of GnRH, the hydroxyl portion of the carboxyl group of glycine has been replaced with an amino group($NH_2$). The abbreviations for the individual amino acid residues above are conventional and are based on the trivial name of the amino acid, e.g. pGlu is pyroglutamic acid, His is histidine, Trp is tryptophan, Ser is serine, Tyr is tyrosine, Gly is glycine, Leu is leucine, Orn is ornithine, Arg is arginine, Lys is lysine, Cys is cysteine, Asn is asparagine, Thr is threonine, Pro is proline, Phe is phenylalanine, Glu is glutamic acid, Asp is aspartic acid and Ala is alanine. Except for glycine, amino acids of the peptides of the invention are of the L-configuration unless noted otherwise.

The substitution of a D-amino acid for Gly in the 6-position of the GnRH decapeptide or nonapeptide provides a GnRH analog having substantially greater binding affinity and thus can be used to produce both agonists and antagonists of higher potency. The substitution of an ethylamide moiety or the like for Gly-$NH_2$ at the C-terminus produces agonists of higher potency. Other substitutions throughout the GnRH decapeptide are known which produce antagonists having an inhibitory effect on the release of LH and other gonadotropins by the pituitary gland of mammalians. Such a releasing or inhibitory effect is obtained when the GnRH analog is administered to a mammalian intravenously, subcutaneously, intramuscularly, orally, percutaneously, e.g. intranasally, intravaginally, or in delayed or timed-release formulations.

There are reasons for desiring to prevent ovulation in female mammalians, and the administration of GnRH analogs that are antagonistic to the normal function of GnRH or of large doses of agonists of GnRH have been used to suppress or delay ovulation. For this reason, such analogs of GnRH are being investigated for their potential use as a contraceptive or for regulating conception periods. GnRH antagonists may also be used for the treatment of precocious puberty and endometriosis. Such antagonists have also been found useful to regulate the secretion of gonadotropins in male mammals and can be employed to arrest spermatogenesis, e.g. as male contraceptives, and for treatment of prostatic hypertrophy.

It is desired to provide improved peptides which are more potent analogs of GnRH.

SUMMARY OF THE INVENTION

The present invention provides improved GnRH analogs some of which are strongly antagonistic to GnRH and have an inhibitory effect on the reproduction processes of mammalians and others which are potent agonists of GnRH.

Generally, in accordance with the present invention, GnRH peptides have been synthesized which have stronger binding efficiency as a result of including a residue having an aliphatic-aromatic ketone side chain in the 6-position, but which can be synthesized economically using relatively inexpensive materials. The GnRH antagonists strongly inhibit the secretion of gonadotropins by the pituitary gland of mammalians, including humans, and/or inhibit the release of steroids by the gonads. These peptides are analogs of GnRH wherein a D-isomer alpha-amino acid having a carboxyl-containing side chain, e.g. D-Glu, D-Hgl or D-Asp, is originally located in the 6-position; the side-chain carboxyl group of this residue is then converted to a mixed alkyl ketone via the formation of a side chain acylium ion intermediate from the carboxyl group, which occurs upon treatment with HF or an equivalent acid, such as a suitable Lewis acid. This mixed alkyl ketone side chain should be one which terminates with an aromatic moiety. By mixed alkyl ketone, for purposes of this application, is meant a ketone which contains one alkyl group and one non-alkyl group. By aromatic, for purposes of this application, is meant a resonant carbocyclic or heterocyclic group, such as that derived from anisole, indole, furan, alkyl pyrrole or thiophene. By Hgl is meant alpha-amino adipic acid, which is also referred to as homoglutamic acid.

In addition, the GnRH antagonists include a 1-position substitution, such as D-pGlu, dehydro-Pro, Pro, halogenated D-Phe, D-Trp or β-(2-naphthyl)-D-alanine(hereinafter β-D-2NAL), a substituted (preferably halogenated) D-Phe in the 2-position, a 3-position substitution, an optional substitution of a diamino acid having not more than 5 carbon atoms in the 4-position, an optional substitution in the 5-position in the form of a halogenated L-Phe, a halogenated L-Tyr or L-Arg and optional substitutions in the 7- and 10-positions. The 1-position substituent, except for D-pGlu, is preferably modified so that its alpha amino group contains an acyl group, such as formyl(For), acetyl(Ac), acrylyl(Acr), vinylacetyl(Vac) or benzoyl(Bz), with Ac and Acr being preferred. Modified D-Trp in the 3-position provides increased antagonistic activity as a result of the specific modifications present in the indole ring. Single substitutions for hydrogen are made in either the 5- or 6-position, and the substitutions are selected from chloro, fluoro, bromo, methyl, amino, methoxy and nitro, with chloro, fluoro and nitro being preferred. The indole nitrogen may also be acylated, e.g. with formyl ($N^{in}$For- or IFor-) or with acetyl. Another 3-position substituent is D-PAL which stands for D-alanine which is substituted by pyridyl on the β-carbon atom with the linkage being to the 2-, 3- or 4-position on the pyridine ring, with D-3PAL being preferred. As mentioned above, the substitutions in the 4-,7- and 10-positions are generally considered to be optional. If substituted, the 10-position is preferably D-Ala-$NH_2$.

Because these peptides are highly potent to inhibit release of LH, they are referred to as GnRH antagonists. The peptides inhibit ovulation of female mammals when administered at very low levels at proestrus and are also effective to cause resorption of fertilized eggs if administered shortly after conception. These peptides are also effective for the contraceptive treatment of male mammals.

The improved GnRH agonists have a similar residue in the 6-position and may have optional substitutions in the 1-position, preferably formyl Pro, and in the 10-position, preferably —$NHCH_2CH_3$(—NHEt).

Other peptide hormones that likewise incorporate such a residue having an aliphatic-aromatic ketone sidechain at a critical generally central location, which results in increased binding affinity to the receptor for that hormone, can be synthesized.

DETAILED DESCRIPTION OF THE PREFERRED EMBODIMENTS

More specifically, the peptides of the present invention from the standpoint of a GnRH antagonist are represented by the following Formula I: X-$R_1$-(W)D-PheR-$R_3$-$R_4$-$R_5$-$R_6$(V)-$R_7$-Arg-Pro-$R_{10}$ wherein X is hydrogen or an acyl group having 7 or less carbon atoms; $R_1$ is dehydro-Pro, Pro, D-pGlu, D-Phe, D-Trp or β-D-NAL; W is F, Cl, $Cl_2$ Br, $NO_2$ or $C^{\alpha}$Me/Cl; $R_3$ is D-Pal, D-Trp, ($N^{in}$For)D-Trp or D-Trp which is substituted in the 5- or 6-position with $NO_2$, $NH_2$, $OCH_3$, F, Cl, Br or $CH_3$; $R_4$ is Ser, Orn, AAL or aBu; $R_5$ is Tyr, Arg, (3F)Phe, (2F)Phe, (3I)Tyr, (3$CH_3$)Phe, (2$CH_3$)Phe, (3Cl)Phe or (2Cl)Phe; $R_6$ is D-Glu, D-Hgl or D-Asp; $R_7$ is Leu, NML, Nle or Nva; $R_{10}$ is Gly-$NH_2$, D-Ala-$NH_2$ or NH-Y, with Y being lower alkyl, cycloalkyl, fluoro lower alkyl or NHCONHQ, where Q is H or lower alkyl; and V is an aromatic moiety portion of a ketone formed from the carboxylic group side chain of $R_6$ and a compound selected from Class Z' consisting of ethylbenzene, propylbenzene, isopropylbenzene, butylbenzene, s-butylbenzene, isobutylbenzene, t-butylbenzene, amylbenzene, 1-methylbutylbenzene, 1-ethylpropylbenzene, 3-methylbutylbenzene, 1,1-dimethylpropylbenzene, hexylbenzene, heptylbenzene, 2-ethylhexylbenzene, octylbenzene, nonylbenzene, decylbenzene, dodecylbenzene, tetradecylbenzene, hexadecylbenzene, octadecylbenzene, cyclopropylbenzene, cyclopentylbenzene, cyclohexylbenzene, (4-acyloxycylohexyl)-benzene, 3-methyl-5-phenyl-cyclohex-2-enone, o-xylene, m-xylene, p-xylene, m-ethyltoluene, p-ethyltoluene, o-propyltoluene, m-propyltoluene, m-cymene, p-propyltoluene, p-cymene, m-s-butyltoluene, p-s-butyltoluene, m-t-butyltoluene, p-dodecyltoluene, p-diethylbenzene, m-t-butylethylbenzene, p-t-butylethylbenzene, m-diisopropylbenzene, p-diisopropylbenzene, p-dibutylbenzene, p-di-s-butylbenzene, p-di-t-butylbenzene, p-di-(1-methylbutyl)benzene, indane(indan or hydrindene), 5-methylindane, 6-t-butyl indane, 2-benzyl indane, dialkyl indane, trialkyl indane, tetraalkyl indane, pentaalkyl indane, hexaalkyl indane, heptaalkyl indane, 1-carboethoxy indane, tetralin, 6-methyl tetralin, 6-ethyl tetrelin, 6-butyl tetralin, 6-hexyl tetralin, 6-cyclohexyl tetralin, dialkyl tetralin, tetraalkyl tetralin, pentaalkyl tetralin, 7-ethyl-1-carboethoxymethyl tetralin, 2-phenyl tetralin, hemimellitene, pseudocumene, mesitylene, prehnitene, isodurene, durene, pentamethylbenzene, ethyl-1,4-xylene, 4-ethyl-1,3-xylene, 2-propyl-1,4-xylene, 2-isopropyl-1,4-xylene, 4-propyl-1,2-xylene, 4-propyl-1,3-xylene, 2-isobutyl-1,4-xylene, 5-6-butyl-1,3-xylene, 2-t-amyl-4-isopropyl-toluene, trialkylbenzene, 4-benzyl-1,3-xylene, 3,4,5,11-tetrahydroacenaphthene, ethylmesitylene, hydrindacene, hydrophenanthrene, pentaalkylbenzene, hydropyrene, hydroanthracene, diphenylmethane, diphenylpropane, bibenzyl, 3,4-diphenylhexane, α,ω-diphenylalkanes, triphenylmethane, paracyclophanes, phenylethylenes, chalkones, formamidotoluene, phenylacetic acid, alkyl phenylacetate, phenylacetonitrile, desoxybenzoin, 1-phenyl-2-nitroethane, 1-phenyl-2-acetamidoethane, alkyl 3-phenylpropionate, 3-phenylpropionitrile, phenylbenzoylalkanes, phenylchloroalkanes, phenylnitroalkanes, alkylphenylbutyrates, haloalkylbenzenes, phenol, phenyl acetate, phenyl propionate, phenyl benzoate, alkylphenols, halophenols, catechol, resorcinol, alkyl resorcinol, pyrogallol, phloroglucinol, trihydroxytoluene, trihydroxyisoamylbenzene, anisole, phenetole, alkylphenylethers, alkyltolylethers, ethylanisole, p-t-butylanisole, m-heptylanisole, p-cyclohexylanisole, anisylhexanes, dimethylanisole, 2-ethyl-4-methylanisole, 5-methoxytetralin, isopropylmethylanisole, hydrophenanthrene, trialkylanisole, fluoroanisole, chloroanisole, chlorophenetole, bromoanisole, bromophenetole, iodoanisole, alkylhaloanisoles, dialkylhaloanisoles, dihaloanisoles, dialkoxyhaloanisoles, guaiacol, resorcinol monomethyl ether, hydroquinone monomethyl ether, alkylhydroxyanisoles, dihydric phenolic dimethyl ethers, polyhydric phenolic methyl ethers, diphenyl ether, alkyldiphenylethers, chlorodiphenyl ethers, alkoxy diphenyl ethers, dialkyldiphenyl ethers, nitrophenylethers, thioanisole, thiophenetole, alkyl phenyl sulfides, o-tolylthioethers, alkylthioanisoles, chlorothioanisole, diphenyl sulfide, nitrodiphenyl sulfide, 2-thiocresol, 3-methoxythiophenol, 3-ethoxythiophenol, diphenyl disulfide, acetanilide(AA) alkyl AA, dialkyl AA, acetamidoindane, acetamidotetralin, trimethyl AA, chloro AA, chloro-4-methyl AA, alkoxy AA, N,N-diacylanilines, nitrobromobenzene, nitrophenol, nitroanisole, nitrophenetole, hydroxy-3-nitrotoluene, nitroresorcinol, nitroanisole, hydroxy-4-nitroanisole, benzoic acid, m-toluic acid, salicylic acid, alkyl salicylates, alkylalkoxy benzoates, alkyl hydroxybenzoates, dimethylacetophenone, trimethylacetophenone, trimethylpropiophenone, methoxyacetophenone, dihydroxyacetophenone, dihydroxypropiophenone, benzophenone, dimethylbenzophenone, dihydroxybenzophenone, biphenyl(BP), alkyl BPs, dialkyl BPs, 9-10-dihydrophenanthrene, chloro BP, bromo BP, hydroxy BP, methoxy BP, methoxy-chloro BP, acetyl BP, nitro BP, chloroacetyl BP, diphenylbenzene, 1,4-terphenyl, 1,3,5-triphenylbenzene, fluorene(F), benzyl F, methoxy F, carbomethoxy F, benzoyl F, naphthalene, alkylnaphthalenes, halonaphthalenes, naphthol, alkylnaphthol ethers, 2-naphtyl methyl sulfide, naphthosultone, 1,8-naphthosultam, naphthalene carboxylic acids, anthracene, alkyl anthracenes, halo anthracenes, alkylhalo anthracenes, alkylalkoxy anthracenes, anthrophenone, 9,9'-bianthryl, phenanthrene(P), alkyl P, halo P, alkoxy P, acetoxy P, hydroxy P, 3-acetamido P, pyrene, 2-methylpyrene, 1-benzoylpyrene, chrysene, 2-ethylchrysene, 6-benzylchrysene, triphenylene, perylene, fluoranthene, biphenylene, furan, alkyl furan, benzofuran(BF), methyl BF, ethyl BF, propyl BF, benzyl BF, phenyl BF, anisyl BF, dihydrobenzofuran, dibenzofuran(DBF), ethyl DBF, propyl DBF, bromo DBF, methoxy DBF, nitro DBF, xanthene, 1-hydroxy-9-oxoxanthene, thiophene, alkylthiophenes, dialkylthiophenes, trialkylthiophenes, 2-benzylthiophene, halothiophenes, dihalothiophenes, trihalothiophenes, alkylhalothiophenes, halophenylthiophene, methyl phenylthiophene, dithienyl, dimethyldithienyl, terthienyl, benzo[b]thiophene(BT), methyl BT, methoxy BT, dibenzothiophene, alkyl pyrrole, dialkyl pyrrole, trialkyl pyrrole, dialkyl-carbomethoxy pyrroles, indole, 2-methylindole, 3-methylindole, 1,2-dimethylindole, 1,2,3-trimethylindole, 2,3,4,6-tetramethylindole, 2-phenylindole, 2,3,dimethyl-1-acetylindole, tetrahydrocarbazole(THC), 9-acetyl THC, 9-benzoyl THC, 6-halo-9-acetyl THC, carbazole, acetyl carbazole, alkyl carbazole, haloalkyl carbazole, benzoyl carbazole, acetylindoline, 1-acyl-2,3-dimethyl-indolines, hexahydrocarbazoles, phenyl pyrazole, phenylalkyl pyrazole, 1-phenyl-3-pyrazolin-5-one(PP), alkyl PP, dialkyl PP, 2-imidazolone (IA), 4-methyl IA, 2-oxo-2,3-dihydrobenzimidazole, imidazo[1,5-a]pyridine(IP), methyl IP, 5,7-dimethyl quinoline, hydroxy quinoline, methoxy quinoline, 2-methylhydroxy quinoline, acyl tetrahydroquinoline, acridan, 10-acetyl acridan, 2-hydroxy-4-methylthiazole, 10-ethyl phenoxazine, 10-acetyl phenoxazine, phenothiazine(PT), 10-alkyl PT, 3,10-dimethyl PT, 10-acyl PT, 1,2-benzisoxazole(BIO), 3-methyl BIO, 7-methoxy BIO and 3-phenyl-7-methoxy BIO.

From the standpoint of a GnRH agonist, the peptides are represented by the Formula IA: $R_1$-His-Trp-Ser-Tyr-$R_6$(V)-Leu-Arg-Pro-$R_{10}$, wherein $R_6$ and V are defined as set forth above and $R_1$ is pGlu or For-Pro and $R_{10}$ is Gly-$NH_2$, D-Ala-$NH_2$ or substituted amide.

By β-D-NAL is meant the D-isomer of alanine which is substituted by naphthyl on the β-carbon atom, which may also be designated 3-D-NAL. Preferably β-D-2NAL is employed which means that the β-carbon atom is attached to naphthalene at the 2-position on the ring structure; however, β-D-1NAL may also be used. Dap represents α, β-diaminopropionic acid, which is also termed β-aminoalanine, and by NML is meant $N^\alpha CH_3$-L-Leu. By AAL is also meant β-amino-Ala and by aBu is meant α, γ diamino butyric acid, either of which or Orn can be present in the 4-position. When Ser is not present in the 4-position, dehydro Pro is preferably present in the 1-position. By $C^\alpha Me$/Cl-D-Phe is meant D-Phe having its α-carbon methylated and being substituted by Cl in the para-position.

The term $R_6$(V) in Formulas I and IA is used to define the D-amino acid residue in the main peptide chain having its side chain carboxyl group modified to form a mixed alkyl ketone. Preferably, the residue in the main chain is D-Glu; however, it may instead be D-Hgl or D-Asp.

The peptides of the present invention can be synthesized by classical solution synthesis or by a solid phase technique using a chloromethylated resin, a benzhydrylamine (BHA) resin, a methylbenzhydrylamine resin (MBHA), an N-alkyl amino methyl resin (NAAM) or any other suitable resin known in the art. When using classical synthesis, it may be advantageous to independently generate the ketone side chain prior to linking the amino acid to the adjacent residues in the peptide chain. Solid phase synthesis is conducted in a manner to stepwise add the amino acids in the chain in the manner set forth in detail in the U.S. Pat. No. 4,211,693. Side-chain protecting groups, as are well known in the art, are preferably added to Ser, Tyr and Arg when present, as well as to certain of the substituents, and may optionally be added to Trp (unless acylated), before these amino acids are coupled to the chain being built upon the resin. When solid phase synthesis is used, the D-Glu, D-Hgl or D-Asp residue in the 6-position is preferably protected with Bzl(benzyl ester), 2,6-dichlorobenzyl(DCB), dinitrophenyl(Dnp), 1-hydroxy-benzotriazole benzl ester(OHbt), 8-hydroxy-quinoline ester-(OHq), p-nitrobenzyloxy(ONBzl), phenylazophenyl or tertiary butoxy; such a synthesis provides the fully protected intermediate peptidoresin.

The intermediates of the invention with respect to a GnRH antagonist may be represented by Formula II:

$X^1$-$R_1$-(W)D-Phe-$R_3(X^2)$-$R_4(X^3)$-$R_5(X^4$ or $X^6)R_6(X^5)$-$R_7$-Arg($X^6$)-Pro-$X^7$ wherein: $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1) acyl-type protecting groups, such as formyl(For), trifluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl (Z), fluorenylmethyloxycarbonyl(FMOC), and substituted benzyloxycarbonyl, such as p-chlorobenzyloxycarbonyl (ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxy-carbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenyl-methyl(trityl) and benzyl(Bzl); (7) trialkylsilane groups, such as trimethylsilane. The preferred α-amino protecting group is Boc when X is hydrogen.

$X^2$ is hydrogen or a protecting group for the indole nitrogen of Trp, such as formyl or benzyl. In many syntheses, there is no need to protect the indole NH of Trp; however $X^2$ is formyl when $R_3$ is ($N^{in}$For)D-Trp. There is no need to protect D-3PAL.

$X^3$ is hydrogen or a protecting group for the alcoholic hydroxyl group of Ser, such as one selected from the group consisting of acetyl, benzoyl, tetrahydropyranyl, tert-butyl, trityl, benzyl and 2,6-dichlorobenzyl, with benzyl being preferred. Alternatively, when a substitution is made for Ser, $X^3$ may be a protecting group for a side chain amino group, such as Tos, Z or ClZ.

$X^4$ is hydrogen or a protecting group for the phenolic hydroxyl group of Tyr, if Tyr is present, selected from the group consisting of tetrahydropyranyl, tert-butyl, trityl, benzyl, Z, 4-bromobenzyloxycarbonyl and 2,6-dichlorobenzyl. 2,6-dichlorobenzyl is preferred.

$X^5$ is a protecting group for the side chain carboxyl group of D-Glu, D-Hgl or D-Asp, selected from the group consisting of Bzl(benzyl ester), 2,6-dichlorobenzyl(DCB), dinitrophenyl(Dnp), 1-hydroxy-benzotriazole benzl ester(OHbt), 8-hydroxy-quinoline ester(OHq), p-nitrobenzyloxy(ONBzl), phenylazophenyl and tertiary butoxy and is preferably Bzl.

$X^6$ is a protecting group for the side chain guanidino group of Arg, such as nitro, Tos, trityl, benzyloxycarbonyl, adamantyloxycarbonyl, Z and Boc or $X^6$ may be hydrogen, which means there is no protection on the side chain group atoms. Tos is generally preferred.

$X^7$ may be Gly-NH-[resin support], D-Ala-NH-[resin support] or N(A)-[resin support]; or it may be amide either of Gly or of D-Ala or a substituted amide attached directly to Pro.

The criterion for selecting side chain protecting groups for $X^2$–$X^6$ is that the protecting group should be stable to the reagent under the reaction conditions selected for removing the α-amino protecting group at each step of the synthesis. The protecting group should not be split off under coupling conditions, and the protecting group should be removable upon completion of the synthesis of the desired amino acid sequence under reaction conditions that will not alter the peptide chain.

When the $X^7$ group is Gly-NH-[resin support] or D-Ala-NH-[resin support], an amide bond connects Gly or D-Ala to BHA resin or to a MBHA resin. When the $X^7$ group is N(A)-[resin support], a substituted amide bond connects Pro to an N-alkylamino methyl resin(-NAAM).

When X is acetyl, for example, at the N-terminus in the final formula, it may be possible to employ it as the $X^1$ protecting group for the α-amino group of D-NAL or whatever amino acid is used in the 1-position by adding it before the coupling of this last amino acid to the peptide chain. However, a reaction is preferably carried out with the peptide on the resin (after deblocking the α-amino group while the side-chain groups remain protected), e.g. by reacting with acetic acid in the presence of dicyclohexyl carbodiimide(DCC) or preferably with acetic anhydride or by another suitable reaction as known in the art.

The fully protected peptide intermediate results from classical solution synthesis and is then deprotected as is well known in the art. Deprotection of the peptide, as well as cleavage of the peptide from a BHA, MBHA or NAAM resin, is effected by treatment with hydrofluoric acid (HF) or its equivalent at a temperature which promotes formation of the acylium ion at the side-chain carboxyl group, preferably between about 20° C. and about 25° C. for an appropriate time, e.g. about 2–3 hours. A sufficient excess of a desired aromatic compound selected from Class Z', such as anisole, which also functions as a scavenger, is added to the peptide prior to treatment with HF. Generally an amount is added at least equal to 20 times the molar amount of the peptide. In the presence of the acylium ion, this added compound from Class Z' reacts to create the aliphatic-aromatic ketone side chain, the mechanism being illustrated in *Solid-Phase Peptide Synthesis*, G. Barany & R. Merrifield, p. 192–197. After the removal of HF under vacuum, the cleaved, deprotected peptide is conveniently treated with ether, decanted, taken-up in dilute acetic acid and lyophilized. At this point, the peptide can, if desired, be converted to its nontoxic salt, as by treatment, for example, with 1 N acetic acid.

Broadly, the invention provides a method of making a peptide hormone of not greater than about fifty residues having a glutamic acid, a homoglutamic acid or an aspartic acid residue at a nonterminus position in the main chain thereof, the side chain of which residue constitutes a mixed alkyl ketone terminating in an aromatic group, which method comprises forming a peptide intermediate wherein said main peptide chain contains a glutamic acid, a homoglutamic acid or an aspartic acid residue in the desired position, the side chain carboxyl group of which is protected with a protecting group selected from the class consisting of Bzl(benzyl ester), 2,6-dichlorobenzyl(DCB), dinitrophenyl(Dnp), 1-hydroxy-benzotriazole benzyl ester(OHbt), 8-hydroxy-quinoline ester(OHq), p-nitrobenzyloxy(ONBzl), phenylazophenyl and tertiary butoxy; treating said peptide intermediate with HF and an aromatic compound selected from Class Z' (as defined herein) under conditions so that said protecting group is removed and an acylium ion intermediate is formed which ion reacts with said aromatic compound to form a mixed alkyl ketone therewith, and removing said HF and recovering said desired peptide hormone which has increased binding affinity to the receptor in question as a result of the inclusion of said aromatic ketone side chain. When making a GnRH nonapeptide or decapeptide, the residue is located in the 6-position.

More specifically, the invention provides a method for making a GnRH antagonist having Formula I or a nontoxic salt thereof, which method comprises (a) forming an intermediate compound having the Formula II:

$X^1$-$R_1$-(W)D-Phe-$R_3$($X^2$)-$R_4$($X^3$)-$R_5$($X^4$ or $X^6$) $R_6$($X^5$)-$R_7$-Arg($X^6$)-Pro-$X^7$ wherein $X^1$ is hydrogen or an α-amino protecting group; $X^2$ is hydrogen or a protecting group for the indole nitrogen; $X^3$ is hydrogen or a protecting group for the alcoholic hydroxyl group of Ser or for a side-chain amino group; $X^4$ is hydrogen or a protecting group for the phenolic hydroxyl group of Tyr; $X^5$ is a protectimg group for a side chain carboxyl group, $X^6$ is hydrogen or a protecting group for a side-chain amino group; and $X^7$ is selected from the group consisting of Gly-NH-(resin support), D-Ala-NH-(resin support), -N(A)-(resin support), Gly-NH$_2$, D-Ala-NH$_2$, and substituted amides, wherein A represents an alkyl group; (b) splitting off one or more of the groups $X^1$ to $X^6$ and/or cleaving from any resin support included in $X^7$ by treatment with HF or its equivalent in an amount equal to about 5 to 15 times the weight of the resin plus a desired compound selected from Class Z' as defined hereinbefore and, if desired, (c) converting a resulting peptide into a nontoxic salt thereof. The molar amount of the compound from Class Z' that is used is preferably at least about 50 times the molar amount of the synthetic peptide which is present.

Similar methods can be used for making GnRH agonists and other peptide hormones of interest which are not more than about 50 residues long and which will exhibit increased binding affinity to the receptor in question as a result of the inclusion of such an aliphatic-aromatic ketone side chain on a nonterminal residue.

Purification of the peptide is effected by ion exchange chromotography on a CMC column, followed by partition chromotography using the elution system: n-butanol;0.1lN acetic acid (1:1 volume ratio) on a column packed with Sephadex G-25, or by using HPLC, as known in the art and reported in Rivier, J. et al., *J. Chromatography*, 288 (1984) 303-328.

The GnRH antagonists of the invention are effective at levels of less than 100 micrograms per kilogram of body weight, when administered at about noon on the day of proestrous, to prevent ovulation in female rats. For prolonged suppression of ovulation, it may be necessary to use dosage levels in the range of from about 0.1 to about 2.5 milligrams per kilogram of body weight. These antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE I

GnRH antagonists as indicated in TABLE I having the formula: Ac-$R_1$-(4Cl)D-Phe-$R_3$-Ser-Tyr-D-Glu(V)-Leu-Arg-Pro-$R_{10}$ are prepared by the solid-phase procedure referred to above, wherein Z' is a compound which results in the desired aromatic moiety portion V of the keto side chain.

TABLE I

| | $R_1$ | $R_3$ | Z' | $R_{10}$ |
|---|---|---|---|---|
| 1 | β-D-2NAL | D-3PAL | $C_6H_5OCH_3$ | D-Ala—$NH_2$,($Arg^5$) |
| 2 | " | D-Trp | " | " |
| 3 | dehydro Pro | β-D-2NAL | " | Gly—$NH_2$,(4F)D-$Phe^2$ |
| 4 | β-D-2NAL | ($6NH_2$)D-Trp | $C_6H_5OH$ | " |
| 5 | " | ($5OCH_3$)D-Trp | $C_6H_4(OH)_2$ | " |
| 6 | " | (5Br)D-Trp | $C_6H_3(CH_3)_2OCH_3$ | " |
| 7 | " | (5F)D-Trp | $C_6H_5SCH_3$ | " |
| 8 | " | (5Cl)D-Trp | $C_5NH_4SH$ | " |
| 9 | Pro | ($5CH_3$)D-Trp | indole | D-Ala—$NH_2$ |
| 10 | β-D-2NAL | ($N^{in}$For)D-Trp | 2-methylindole | " |
| 11 | " | D-3PAL | 3-methylindole | " |
| 12 | Pro | (5Cl)D-Trp | " | " |
| 13 | dehydro Pro | ($6NO_2$)D-Trp | " | $NHCH_2CH_3$ |
| 14 | D-Trp | (5F)D-Trp | " | " |
| 15 | D-pGlu | D-2PAL | " | D-Ala—$NH_2$ |
| 16 | D-Phe | ($6NO_2$)D-Trp | " | $NHCH_2CH_2CH_3$ |

For purposes of an example, a representative solid phase synthesis of Peptide No. 1 above, which is referred to as [Ac-β-D-$2NAL^1$, (4Cl)D-$Phe^2$, D-$3PAL^3$, $Arg^5$, D-$Glu^6(C_6H_4OCH_3)$, D-$Ala^{10}$]-GnRH is set forth hereinafter. This peptide has the following formula: Ac-β-D-2NAL-(4Cl)D-Phe-D-3PAL-Ser-Arg-D-Glu($C_6H_4OCH_3$)-Leu-Arg-Pro-D-Ala-$NH_2$. The other peptides are similarly synthesized and purified.

A BHA resin is used, and Boc-protected D-Ala is comupled to the resin over a 2-hour period in $CH_2Cl_2$ using a 3-fold excess of Boc derivative and DCC as an activating reagent. The D-alanine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | Isopropyl alcohol + 1% ethanedithiol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc—amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30-300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

After step 13, if the synthesis is manual, an aliquot may be taken for a ninhydrin test: if the test is negative, go back to step 1 for coupling of the next amino acid; if the test is positive or slightly positive, go back and repeat steps 9 through 13.

The above schedule is generally used for coupling of each of the amino acids of the peptide of the invention after the first amino acid has been attached. $N^\alpha$Boc protection is used for each of the remaining amino acids throughout the synthesis. $N^\alpha$Boc-β-D-2NAL is prepared by a method known in the art, e.g. as described in detail in U.S. Pat. No. 4,234,571, issued Nov. 18, 1980. The side chain of Arg is protected with Tos. OBzl is used as a side chain protecting group for the hydroxyl group of Ser, and Bzl is used to protect D-Glu. D-3PAL is left unprotected. $N^\alpha$Boc-β-D-2NAL is introduced as the final amino acid. Boc-Arg(Tos), which has low solubility in $CH_2Cl_2$, is coupled using a DMF:$CH_2Cl_2$ mixture.

After deblocking the α-amino group at the N-terminal, its acetylation is achieved using a large excess of acetic anhydride in dichloromethane. The cleavage of the peptide from the resin and complete deprotection of the side chains is carried out at 24° C. with HF for about 2-½ hours. A scavenger as set forth in the TABLE is added prior to HF treatment to produce the mixed alkyl ketone. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3M NH$_4$OAc in 50/50 methanol/water) followed by partition chromatography in a gel filtration column using the elution system: n-Butanol; 0.1N Acetic acid (1:1—volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]_D^{22} = -28.77° \pm 1 (c=1, 50\%$ acetic acid).

The remaining GnRH antagonists set forth in TABLE 1 are synthesized using the method specified above and an appropriate resin.

Each of the peptides is assayed in vivo to determine its effectiveness to prevent ovulation in female rats. In this test, a specified number of mature female Sprague-Dawley rats, i.e. seven, each having a body weight from 225 to 250 grams, is injected subcutaneously with a specified microgram dosage of peptide in corn oil at about noon on the day of proestrus. Proestrus is the afternoon of ovulation. A separate female rat group is used as a control to which the peptide is not administered. Each of the control female rats ovulates on the evening of proestrus; of the rats treated, the number of them which ovulate is recorded. Each of the peptides set forth in Table I is considered to be significantly effective to prevent ovulation of female rats at a very low dosage, and each peptide is considered to be totally effective at a dose of about five micrograms.

EXAMPLE II

Peptides as indicated in TABLE II having the formula: Ac-β-D-2NAL-(W)D-Phe-D-Trp-R$_4$-R$_5$-R$_6$(V)-R$_7$-Arg-Pro-Gly-NH$_2$ are prepared by the solid phase procedure referred to above, wherein Z' is employed to produce V.

TABLE II

| | W | R$_4$ | R$_5$ | R$_6$ | Z' | R$_7$ |
|---|---|---|---|---|---|---|
| 17 | 4F | Ser | Tyr | D-Glu | C$_6$H$_5$OCH$_3$ | Leu |
| 18 | 4Br | " | (2F)Phe | D-Asp | " | Nle |
| 19 | " | AAL | Tyr | " | C$_6$H$_5$C$_7$H$_{15}$ | Nva |
| 20 | 4Cl | aBu | " | D-Hgl | m-xylene | Nle |
| 21 | " | Ser | Arg | " | p-cymene | " |
| 22 | " | " | (2CH$_3$)Phe | " | p-dibutyl-benzene | Nva |
| 23 | 4F | " | " | D-Asp | indane | NML |
| 24 | " | " | (3CH$_3$)Phe | " | diethyl-indane | " |
| 25 | " | " | (2Cl)Phe | D-Glu | diphenyl-methane | " |
| 26 | 4NO$_2$ | " | Arg | " | C$_6$H$_5$(OH)$_2$ | " |
| 27 | " | Orn | Tyr | " | tetralin | Nle |
| 28 | 2,4Cl$_2$ | Ser | (3F)Phe | " | iodo-benzene | " |

TABLE II-continued

| | W | R$_4$ | R$_5$ | R$_6$ | Z' | R$_7$ |
|---|---|---|---|---|---|---|
| 29 | " | AAL | " | " | chloro-phenol | Nva |
| 30 | C$^\alpha$Me/Cl | Ser | (3I)Tyr | " | 1-phenyl-2-nitroethane | " |
| 31 | 3,4Cl$_2$ | Orn | (3Cl)Phe | " | 2-thiocresol | Leu |

In vitro and/or in vivo testing of the peptides specified in Table II shows that the peptides listed in Table II are considered effective to block GnRH-induced LH secretion in vitro at a reasonable concentration. Many of these peptides are more potent in vivo than the present standard. All of the peptides are considered to be effective to prevent ovulation of female mammals at very low dosages.

EXAMPLE III peptides as indicated in TABLE III having the formula: X-β-D-2NAL-(4Cl)D-Phe-(1 For)D-Trp-Ser-R$_5$-D-Glu(V)-NML-Arg-Pro-R$_{10}$ are prepared by the solid-phase procedure referred to above using an appropriate resin, wherein Z' is employed to produce V.

TABLE III

| | X | R$_5$ | Z' | R$_{10}$ |
|---|---|---|---|---|
| 32 | Ac | Tyr | thioanisole | Gly—NH$_2$ |
| 33 | Acr | " | diphenyl ether | D-Ala—NH$_2$ |
| 34 | For | Arg | triethyl anisole | NHCH$_2$CH$_3$ |
| 35 | Bz | (3F)Phe | chlorophenetole | NHCH$_3$ |
| 36 | Ac | (2F)Phe | acetanilide | NHCF$_3$ |
| 37 | Vac | (2Cl)Phe | nitroanisole | NHCH$_2$CH$_2$CH$_3$ |
| 38 | Acr | (3Cl)Phe | methyltolylether | NHCF$_2$CF$_3$ |
| 39 | Ac | (3F)Phe | pyrogallol | D-Ala—NH$_2$ |
| 40 | Acr | (3I)Tyr | salicylic acid | " |
| 41 | Ac | Tyr | benzoic acid | " |
| 42 | " | (3Cl)Phe | benzoic acid | Gly—NH$_2$ |
| 43 | Vac | " | biphenyl | NHNHCONH$_2$ |
| 44 | Bz | Arg | diphenylbenzene | NHNHCONHCH$_3$ |

In vitro and/or in vivo testing of the peptides specified in Table III shows that the peptides listed in Table III are considered effective to block GnRH-induced LH secretion in vitro at a reasonable concentration. Many of these peptides are more potent in vivo than the present standard. All of the peptides are considered to be effective to prevent ovulation of female mammals at very low dosages.

EXAMPLE IV

Peptides as indicated in TABLE IV having the formula: Ac-R$_1$-(4F)D-Phe-R$_3$-Ser-Tyr-R$_6$(V)-Leu-Arg-Pro-NHCH$_2$CH$_3$ are prepared by the solid-phase procedure referred to above, wherein Z' is used to Produce V.

TABLE IV

| | R$_1$ | R$_3$ | R$_6$ | Z' |
|---|---|---|---|---|
| 45 | dehydro Pro | β-D-2NAL | D-Glu | methoxy biphenyl |
| 46 | " | " | D-Asp | fluorene |
| 47 | " | " | D-Hgl | anthracene |
| 48 | " | " | D-Glu | phenanthrene |
| 49 | β-D-1NAL | D-3PAL | D-Asp | indole-acetate salt |
| 50 | " | D-2PAL | D-Glu | furan |
| 51 | Pro | " | " | methylbenzofuran |
| 52 | D-Trp | " | D-Hgl | methyldibenzofuran |
| 53 | D-Phe | " | D-Asp | chlorothiophene |
| 54 | Pro | D-4PAL | D-Hgl | propyl pyrrole |
| 55 | " | " | " | acetyl carbazole |
| 56 | D-pGlu | " | D-Glu | phenothiazine |

In vitro and/or in vivo testing of the peptides specified in Table IV shows that the peptides listed in Table IV are considered effective to block GnRH-induced LH secretion in vitro at a reasonable concentration. Many of these peptides are more potent in vivo than the present standard. All of the peptides are considered to be effective to prevent ovulation of female mammals at very low dosages.

EXAMPLE V

GnRH agonists as indicated in TABLE V having the formula: pGlu-His-Trp-Ser-Tyr-$R_6$(V)-Leu-Arg-Pro-$R_{10}$ are prepared by the solid-phase procedure referred to above, wherein Z' is used to produce V.

TABLE V

| | $R_6$ | Z' | $R_{10}$ |
|---|---|---|---|
| 57 | D-Glu | $C_6H_4OCH_3$ | $NHCH_2CH_3$ |
| 58 | " | " | Gly—$NH_2$ |
| 59 | D-Asp | " | D-Ala—$NH_2$ |
| 60 | " | $C_6H_4OH$ | Gly—$NH_2$ |
| 61 | D-Hgl | acridan | " |
| 62 | " | 1,2-benzisoxazole | Gly—$NH_2$ (formyl Pro[1]) |
| 63 | " | phenothiazine | " |
| 64 | " | 2-imidazolone | " |
| 65 | " | indole | D-Ala—$NH_2$ |
| 66 | " | 1,2-dimethylindole | " |
| 67 | " | 2-phenylindole | D-Ala—$NH_2$ (formyl Pro[1]) |
| 68 | D-Glu | tetrahydrocarbazole | " |
| 69 | " | hydroxyquinoline | $NHCH_2CH_3$ |
| 70 | D-Asp | resorcinol | " |
| 71 | " | phehnitene | D-Ala—$NH_2$ |
| 72 | D-Glu | durene | " |

To synthesize peptide No. 57, an N-ethylamine resin is used which is prepared by reacting a cross-linded chloromethylated polystyrene resin with ethylamine at 4° C. for about 2 days and Boc-protected Pro is coupled to the resin over a 2-hour period in $CH_2Cl_2$ using a 3-fold excess of Boc derivative and DCC as an activating reagent. The proline residue attaches to the NEAM resin by a substituted amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | Isopropyl alcohol + 1% ethanedithiol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc—amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

$N^\alpha$Boc protection is used for each of the remaining amino acids throughout the synthesis, except for pGlu which is left unprotected; however, it can optionally be protected with Z. The side chain of Arg is protected with Tos. OBzl is used as a side chain protecting group for the hydrozyl group of Ser, and Bzl is used to protect D-Glu. Trp is left unprotected. pGlu is introduced as the final amino acid. Boc-Arg(Tos) and Boc-Trp, which have low solubility in $CH_2Cl_2$, are coupled using $DMF:CH_2Cl_2$ mixtures.

After deblocking the α-amino group at the N-terminus, its acetylation is achieved using a large excess of acetic anhydride in dichloromethane. The cleavage of the peptide from the resin and complete deprotection of the side chains is carried out at 24° C. with HF for about 2-½ hours. The compound Z' as set forth in the TABLE V is added prior to HF treatment to produce the mixed alkyl ketone and in most cases to act as a scavenger. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3M NH$_4$OAc in 50/50 methanol/water) followed by partition chromatography in a gel filtration column using the elution system: n-Butanol; 0.1N Acetic acid (1:1—volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain.

The remaining GnRH agonists set forth in TABLE V are synthesized using the method specified above and an appropriate resin.

Each of the peptides is assayed in vitro to determine its effectiveness to cause the secretion of LH from a primary culture of dispersed rat pituitary cells using the procedure set forth in U.S. Pat. No. 4,382,922. Each of the peptides set forth in Table V is considered to be very significantly more potent effective than native GnRH, and each peptide is considered to be totally effective at a reasonable dose to regulate fertility and to treat patients having precocious puberty, endometriosis or dysmenorrhea.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. An aqueous solution of the peptide is repeatedly treated, for example, with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of GnRH.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation or chemotherapy. Effective dosages will vary with the form of administration and the particular species of mammal being treated. An example of one typical dosage form is a bacteriostatic water solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. For instance, instead of the residues specified for $R_{10}$, Sar-NH$_2$ (Sar=sarcosine) can be used, or NH-Y can be present, with Y being lower alkyl, cycloalkyl, fluoro lower alkyl or NHCONHQ, where Q is H or lower alkyl, all of the foregoing being considered to be equivalents. D-Phe in the 1-position can be optionally halogenated as specified with respect to the 2-position substitution. In addition to the compounds enumerated as comprising Class Z', additional equivalent aromatic compounds are identified in Volume 3, *Aromatic Ketone Synthesis*, Peter H. Gore, 1963, Interscience Publishers. Other equivalent residues, such as Met, Cys, Phe, Tyr and Trp can be used instead of those hereinbefore specified in the 7-position.

Particular features of the invention are emphasized in the claims that follow.

What is claimed is:

1. A peptide or a nontoxic salt thereof, said peptide having the formula: X-$R_1$-$R_2$-$R_3$-$R_4$-$R_5$-D-Glu($C_6H_4OCH_3$)-$R_7$-Arg-Pro-$R_{10}$ wherein X is hydrogen or an acyl group having 7 or less carbon atoms; $R_1$ is pGlu, dehydro-Pro, Pro, D-pGlu, D-Phe, D-Trp or β-D-NAL; $R_2$ is His or (W)D-Phe where W is 4F, 4Cl$_2$, 2,4Cl$_2$, 4Br, 4NO$_2$ or C$^\alpha$Me/4Cl; $R_3$ is Trp, D-Trp, β-D2NAL, D.PAL,(N$^{im}$For)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl))Phe or (2ClPhe; $R_7$ is Leu, NML, Nle or Nva; $R_{10}$ is Gly-NH$_2$, D-Ala-NH$_2$ or NH-Y, with Y being lower alkyl, cycloalkyl, fluoro lower alkyl or NHCONHQ, where Q is H or lower alkyl.

2. A peptide in accordance with claim 1 having the formula: Ac-β-D-2NAL-(4Cl)D-Phe-D-3PAL Ser-Arg-D-Glu($C_6H_4OCH_3$)-Leu-Arg-Pro-D-Ala-NH$_2$.

3. A peptide in accordance with claim 1 having the formula: Ac-dehydro Pro-(4F)D-Phe-β-D-2NAL-Ser-Tyr-D-Glu($C_6H_4OCH_3$)-Leu-Arg-Pro-Gly-NH$_2$.

4. A peptide in accordance with claim 1 having the formula: pGlu-His-Trp-Ser-Tyr-D-Glu($C_6H_4OCH_3$)-Leu-Arg-Pro-Gly-NHCH$_2$CH$_3$.

* * * * *

UNITED STATES PATENT AND TRADEMARK OFFICE
CERTIFICATE OF CORRECTION

PATENT NO. : 4,677,193

DATED : June 30, 1987

INVENTOR(S) : Jean E. F. Rivier, Harry A. Anderson and Wylie W. Vale, Jr.

It is certified that error appears in the above-identified patent and that said Letters Patent is hereby corrected as shown below:

Column 9, line 10, change "0.11N" to --0.1N--.

Column 9, line 67, correct the spelling of --coupled--.

Column 12, line 20, change "peptides" to --Peptides--.

Column 13, line 34, correct the spelling of --cross-linked--.

Column 14, line 6, correct the spelling of --hydroxyl--.

Column 16, line 20, change ":" to --;--.

Column 16, lines 20-21, change "$4Cl_2$, $2,4Cl_2$" to --$4Cl$, $3,4Cl_2$, $2,4Cl_2$--.

Column 16, line 22, change "D.PAL" to --D-PAL--.

Column 16, line 26, change "(3Cl))Phe" to --(3Cl)Phe--.

Column 16, line 26, change "(2ClPhe" to --(2Cl)Phe--.

Signed and Sealed this

Tenth Day of November, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,677,193
DATED : June 30, 1987
INVENTOR(S) : Jean E. F. Rivier et al.

It is certified that error appears in the above-identified patent and that said Letters Patent is hereby corrected as shown below:

Column 16, line 39, change "Leu-Arg-Pro-Gly-$NHCH_2$-$CH_3$" to read --Leu-Arg-Pro-$NHCH_2$-$CH_3$--.

Signed and Sealed this

Thirteenth Day of June, 1989

Attest:

DONALD J. QUIGG

Attesting Officer

Commissioner of Patents and Trademarks